United States Patent [19]

L'Eplattenier et al.

[11] 3,963,708

[45] June 15, 1976

[54] BIS-AZOMETHINE METAL COMPLEX COLORANTS FROM HYDROXYCOUMARIN DERIVATIVES OR HYDROXYCHROMONE DERIVATIVES

[75] Inventors: Francois L'Eplattenier; Laurent Vuitel, both of Therwill; Andre Pugin, Riehen, all of Switzerland

[73] Assignee: Ciba-Geigy Corporation, Ardsley, N.Y.

[22] Filed: July 28, 1975

[21] Appl. No.: 599,445

[30] Foreign Application Priority Data
July 31, 1974 Switzerland.................... 10584/74

[52] U.S. Cl............................ 260/240 G; 260/343.5; 260/429 C
[51] Int. Cl.²........................................ C07D 493/04
[58] Field of Search......... 260/240 G, 343.5, 429 C, 260/240 R

[56] References Cited
UNITED STATES PATENTS

| | | | |
|---|---|---|---|
| 3,388,141 | 6/1968 | Berenbaum..................... | 260/429 C |
| 3,864,371 | 2/1975 | Inman et al..................... | 260/429 C |
| 3,896,113 | 7/1975 | Kaul............................... | 260/240 G |

FOREIGN PATENTS OR APPLICATIONS

| 634,236 | 3/1950 | United Kingdom.............. 260/343.5 |
|---|---|---|

*Primary Examiner*—Allen B. Curtis
*Attorney, Agent, or Firm*—Vincent J. Cavalieri

[57] ABSTRACT

Bis-azomethine metal complex colorants of the formulae

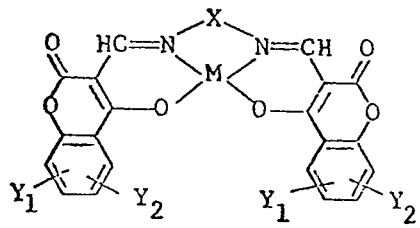

or

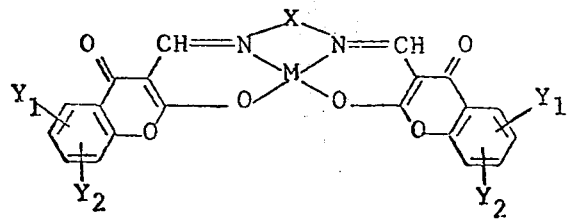

wherein M denotes a divalent transition metal cation, zinc ion or cadmium ion, X denotes an isocyclic or heterocyclic aromatic radical to which the two nitrogen atoms are bonded in the o- or peri-position to one another and $Y_1$ and $Y_2$ denote hydrogen, halogen, alkyl, aryl, nitro, alkoxy, phenoxy or hydroxyl, which are suitable for pigmenting high-molecular organic material.

10 Claims, No Drawings

BIS-AZOMETHINE METAL COMPLEX COLORANTS FROM HYDROXYCOUMARIN DERIVATIVES OR HYDROXYCHROMONE DERIVATIVES

It has been found that new valuable bis-azomethine metal complex colorants of the formulae

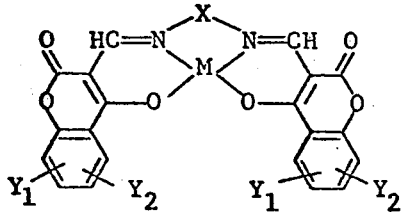

(Ia)

or

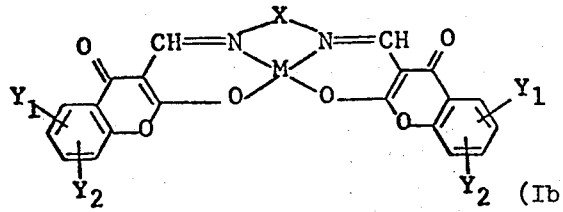

(Ib)

wherein M denotes a divalent transition metal cation, zinc ion or cadmium ion, X denotes an isocyclic or heterocyclic aromatic radical, to which the two nitrogen atoms are bonded in the o-position or peri-position to one another, and $Y_1$ and $Y_2$ denote hydrogen, halogen, alkyl, aryl, nitro, alkoxy, phenoxy or hydroxyl, are obtained when a 4-hydroxycoumarin derivative or, as its tautomeric form, a 2-hydroxychromone derivative (for simplicity, only the first tautomeric form is mentioned in the text), of the formulae

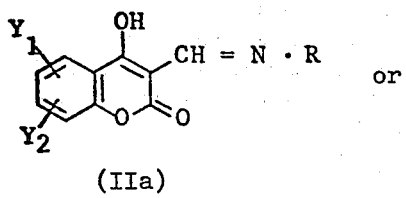

(IIa)

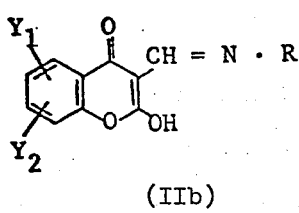

(IIb)

wherein R denotes alkyl or aryl, or of the formulae

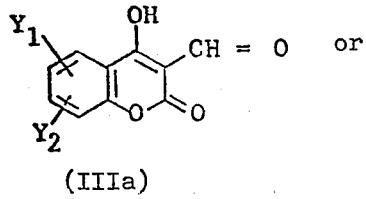

(IIIa)

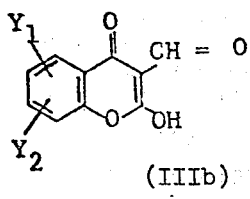

(IIIb)

is reacted with a diamine of the formula $$H_2N - X - NH_2 \qquad (IV)$$

and a compound which donates a divalent transition metal cation, zinc ion or cadmium ion.

Colorants of particular interest are those of the formulae

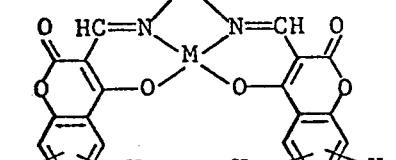

(Va)

or

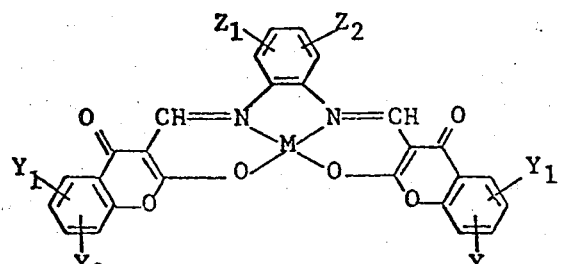

(Vb)

wherein M denotes a divalent nickel, copper, zinc or cadmium ion, $Y_1$ and $Y_2$ denote hydrogen, chlorine, alkyl with 1–6 carbon atoms or alkoxy with 1–6 carbon atoms and $Z_1$ and $Z_2$ denote hydrogen, halogen, alkyl with 1–6 carbon atoms, alkoxy with 1–6 carbon atoms, aryloxy, arylalkyl with 7–10 carbon atoms, trifluoromethyl or phenylcarbamoyl, phenylsulphamoyl, carbalkoxy, carboxyl, alkanoyl, aroylamino or nitro, or wherein the two radicals $Z_1$ and $Z_2$ form a fused benzene ring or hetero-ring.

Colorants of particular interest are those of the formulae Va or Vb, in which $Y_1$ and $Y_2$ denote hydrogen and/or $Z_1$ and $Z_2$ denote hydrogen, trifluoromethyl or chlorine, and M represents nickel.

Possible starting materials are the 4-hydroxycoumarin compounds of the formula II and III, where R preferably denotes aryl, especially phenyl, or phenyl substituted by alkyl, aryl, alkoxy or halogen, and $Y_1$ and $Y_2$ preferably denote hydrogen, chlorine, alkyl with 1–6 carbon atoms or alkoxy with 1–6 carbon atoms.

The manufacture of the aldehyde of 4-hydroxycoumarin of the formula III, which serves as the starting material, is generally known. The corresponding aldimine is preferably manufactured either by reaction of the 4-hydroxycoumarin with a diarylformamidine or with a formic acid ortho-ester and an aromatic amine. In general, the formation of the Schiff's bases proceeds with very good yields.

Preferably, aromatic o-diamines of the formula IV are used, especially those of the formula

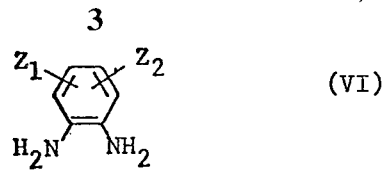

wherein $Z_1$ and $Z_2$ have the abovementioned meaning.

The following may be mentioned as examples of diamines to be used: 1,2-phenylenediamine, 4-chloro-1,2-phenylenediamine, 4,5-dichloro-1,2-phenylenediamine, 4-methyl-1,2-phenylenediamine, 4,5-dimethyl-1,2-phenylenediamine, 3,5-dimethyl-1,2phenylenediamine, 4-methoxy-1,2-phenylenediamine, 4,5-dimethoxy-1,2-phenylenediamine, 4-trifluoromethyl-1,2-phenylenediamine, 4-phenylisopropyl-1,2-phenylenediamine, 1,2-diaminonaphthalene, 2,3-diaminonaphthalene, 1,8-diaminonaphthalene, 1,2-diaminoanthraquinone, 2,3-diaminoanthraquinone, 2-methyl-5,6-diaminobenzimidazole, 1-methyl-5,6-diaminobenzimidazol-2-one, 4-phenoxy-1,2-phenylenediamine, 4-methylsulphonyl-1,2-phenylenediamine, 4-ethylsulphonyl-1,2-phenylenediamine, 4-carboxy-1,2-phenylenediamine, 4-methoxycarbonyl-1,2phenylenediamine, 4-ethoxycarbonyl-1,2-phenylenediamine, 4-cyano-1,2-phenylenediamine, 4-acetylamino-1,2-phenylenediamine, 4-benzoylamino-1,2-phenylenediamine, 4-nitro-1,2-phenylenediamine, 4-methoxy-5-chloro-1,2-phenylenediamine, 4-methyl-5-chloro-1,2-phenylenediamine, 4-ethyl-1,2-phenylenediamine, 3,4-diaminopyridine, 2,3-diaminoquinoxaline, 5,6-diaminobenzimidazol-2-one, 6,7-diamino-2,3-dihydroxyquinoxaline and 6,7-diamino-2,3-dihydrophthalazine-1,4-dione.

Examples of compounds which donate a divalent metal ion are the acetate, stearate, chloride, sulphate, nitrate and phosphate or nickel, copper, zinc and cadmium.

The condensation of the 3-aldimino- or 3-formyl-4-hydroxycoumarin derivative with the diamine to give the azolmethine compound, and its metallisation, are suitably carried out in a one-pot process in an organic solvent. If a 3-formyl-4-hydroxycoumarin derivative is used as the starting material, the condensation to give the azomethine compound and its metallisation can also be carried out independently of one another. Examples of solvents which may be mentioned are methylcellosolve, glacial acetic acid, dimethylformamide, ethylene glycol and carbitol.

The reaction takes place at an elevated temperature, preferably between 50°C and the boiling point of the solvent used.

Since the metal complexes obtained are sparingly soluble in the solvents mentioned, they can easily be isolated by filtration. Any impurities can be removed by elution.

The new colorants are valuable pigments which can be used, in a finely divided form, for pigmenting high molecular organic material, for example cellulose ethers and cellulose esters, such as ethylcellulose, cellulose acetate, cellulose butyrate, natural resins or synthetic resins, such as polymerisation resins or condensation resins, for example aminoplasts, especially urea-formaldehyde and melamine-formaldehyde resins, alkyd resins, phenoplasts, polycarbonates, polyesters, polyamides or polyurethanes, polyolefines, such as polyethylene or polypropylene, polyvinyl chloride, polystyrene, polyacrylonitrile, polyacrylic acid esters, rubber, casein, silicones, and silicone resins, individually or as mixtures.

For these purposes it is immaterial whether the high-molecular compounds mentioned are in the form of plastic masses or melts or in the form of spinning solutions, lacquers, paints or printing inks. Depending on the end use, it proves advantageous to use the new pigments as toners or in the form or preparations.

In addition to the pure pigment, the preparations can, for example, also contain natural resins, such as abietic acid or its esters, ethylcellulose, cellulose acetobutyrate, alkaline earth metal salts of higher fatty acids, fatty amines, such as stearylamine or rosin-amine, vinyl chloride/vinyl acetate copolymers, polyacrylonitrile or polyterpene resins or water-soluble dyestuffs, for example dyestuffsulphonic acids or their alkaline earth metal salts.

The new colorants are distinguished by good fastness to light and to weathering.

In the examples which follow, the parts, unless stated otherwise, denote parts by weight. The relationship of parts by weight to parts by volume is as of the gram to the cubic centimetre.

EXAMPLE 1 a.

16.2 Parts of 4-hydroxycoumarin, 14.8 parts of orthoformic acid triethyl ester and 9.3 parts of aniline are initially introduced into 100 parts by volume of ethylene glycol. The stirred suspension is brought into solution at 150°C, and the solution is slowly warmed to 180°C and stirred at this temperature for 20 minutes. After cooling to 130°C, 50 parts by volume of methylcellosolve are added to the solution and the residue is filtered off at room temperature, washed with alcohol and then dried in vacuo at 80°C. 23.7 parts (89% of theory) of 4-hydroxy-3-N-phenylaldiminecoumarin are obtained.

| Microanalysis: | % | C | H | N |
|---|---|---|---|---|
| | Calculated | 72.44 | 4.17 | 5.27 |
| | Found | 72.30 | 4.10 | 5.30 | b.

18.6 Parts of the resulting 4-hydroxy-3-N-phenylaldimine-coumarin, 3.78 parts of o-phenylenediamine and 8.72 parts of nickel acetate tetrahydrate in 600 parts by volume of methylcellosolve are stirred for 3 hours at 100°C. The orange precipitate is filtered off at 60°C, washed with alcohol and acetone and dried. 17.4 g (98% of theory) of the analytically pure nickel complex are obtained.

| Microanalysis: | % | C | H | N | Ni |
|---|---|---|---|---|---|
| | Calculated | 61.3 | 2.8 | 5.5 | 11.5 |
| | Found | 61.2 | 2.7 | 5.6 | 11.5 | c.

If the procedure indicated in Example 1b is followed but instead of 4-hydroxy-3-N-phenylaldimine-coumarin, 4-hydroxy-3-formylcoumarin is used, a Ni complex of the same composition as that indicated in Example 1b is obtained. (Yield, 90% of theory).

EXAMPLES 2–13

The metal complexes of the general formula

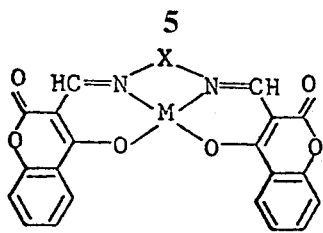

or

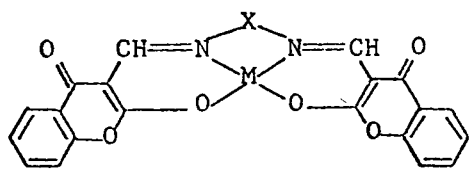

listed in Table 1 were prepared analogously to Example 1b.

Table 1

| Example No. | X | $M^{-2}$ | Yield | Shade in PVC |
|---|---|---|---|---|
| 2 | (o-tolyl) | Cu | 87% | olive |
| 3 | (3,4-dimethylphenyl, CH₃) | Ni | 96% | yellow |
| 4 | (OCH₃-phenyl) | Ni | 68% | olive |
| 5 | (CF₃-phenyl) | Ni | 93% | yellow |
| 6 | (H₃C-C(CH₃)-diphenyl) | Ni | 86% | yellow |
| 7 | (H₃C-C(CH₃)-diphenyl) | Cu | 91% | green-yellow |
| 8 | (biphenyl) | Ni | 94% | yellow |
| 9 | (phenoxyphenyl) | Ni | 89% | yellow |

Table 1-continued

| Example No. | X | $M^{-2}$ | Yield | Shade in PVC |
|---|---|---|---|---|
| 10 | (Cl, Cl-phenyl) | Ni | 100% | brown-yellow |
| 11 | (benzimidazolone N-CH₃) | Ni | 38% | brown-orange |
| 12 | (2-methylbenzimidazole) | Ni | 89% | yellow |
| 13 | (H₃CO, OCH₃-phenyl) | Ni | 35% | brown |
| 14 | —(CH₂)₂— | Ni | 78% | yellow |

EXAMPLES 15–21

The nickel complexes of the formula

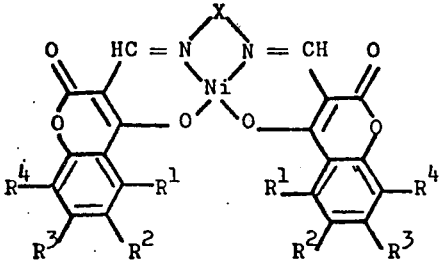

listed in Table 2 were manufactured analogously to Example 1b.

Table 2

| No. | $R^1$ | $R^2$ | $R^3$ | $R^4$ | X | Yield | Shade in PVC |
|---|---|---|---|---|---|---|---|
| 15 | H | H | H | H | (H₃CO, Cl-phenyl) | 73% | yellow |
| 16 | H | CH₃ | H | H | (phenyl) | 85% | yellow |
| 17 | H | CH₃ | H | H | (CF₃-phenyl) | 93% | yellow |
| 18 | H | Cl | H | H | (phenyl) | 69% | yellow |

Table 3

| No. | R¹ | R² | R³ | R⁴ | X | Yield | Shade in PVC |
|---|---|---|---|---|---|---|---|
| 22 | H | H | H | H | 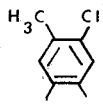 | 96% | yellow |
| 23 | H | CH₃ | H | H | 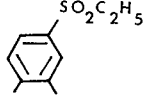 | 95% | yellow |
| 24 | H | H | H | H | 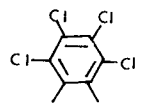 | 93% | orange |
| 25 | H | H | H | H | 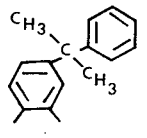 | 81% | yellow |

Table 2-continued

| No. | R¹ | R² | R³ | R⁴ | X | Yield | Shade in PVC |
|---|---|---|---|---|---|---|---|
| 19 | H | Cl | H | H |  | 34% | yellow |
| 20 |  | | H | H |  | 55% | brown-yellow |
| 21 | H | Cl | H | Cl |  | 93% | yellow |

EXAMPLES 22–25

The nickel complexes of the formula

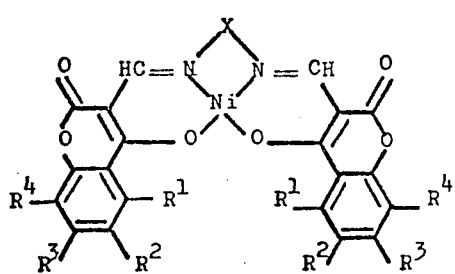

listed in Table 3 were manufactured analogously to Example 1c.

What we claim is:

1. Bis-azomethine metal complex colorants of the formulae

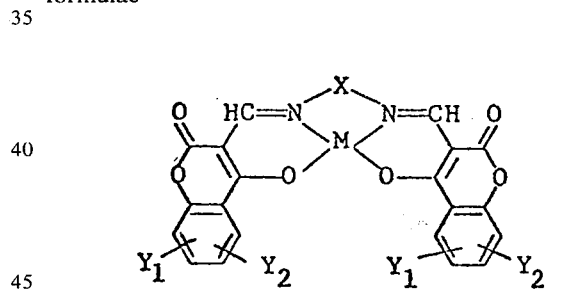

or

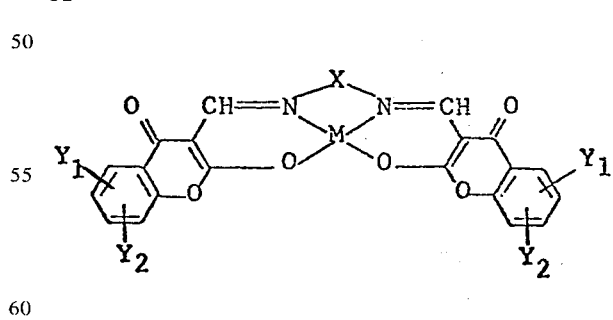

wherein M denotes a divalent transition metal cation, zinc ion or cadmium ion, X denotes an isocyclic or heterocyclic aromatic radical to which the two nitrogen atoms are bonded in the o- or peri-position to one another and Y₁ and Y₂ denote hydrogen, halogen, alkyl, aryl, nitro, alkoxy, phenoxy or hydroxyl.

2. Bis-azomethine metal complex colorants according to claim 1, of the formula

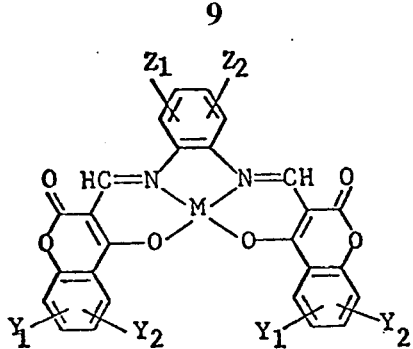

or

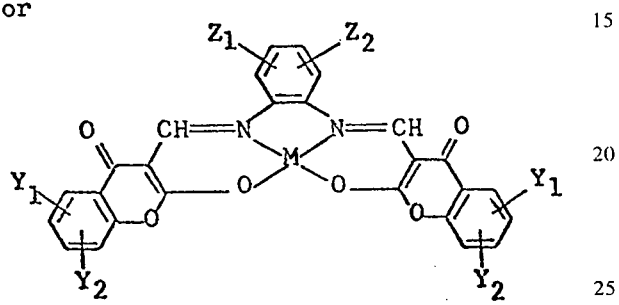

wherein M denotes a divalent nickel, copper, zinc or cadmium ion, $Y_1$ and $Y_2$ denote hydrogen, chlorine, alkyl with 1-6 carbon atoms or alkoxy with 1-6 carbon atoms and $Z_1$ and $Z_2$ denote hydrogen, halogen, alkyl with 1-6 carbon atoms, alkoxy with 1-6 carbon atoms, aryloxy, arylalkyl with 7-10 carbon atoms, trifluoromethyl or phenylcarbamoyl, phenylsulphamoyl, carbalkoxy, carboxyl, alkanoyl, aroylamino or nitro, or wherein the two radicals $Z_1$ and $Z_2$ form a fused benzene ring or hetero-ring.

3. Bis-azomethine metal complex colorants according to claim 2, of the formula

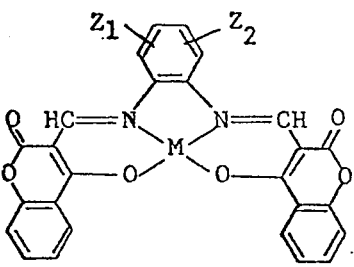

or

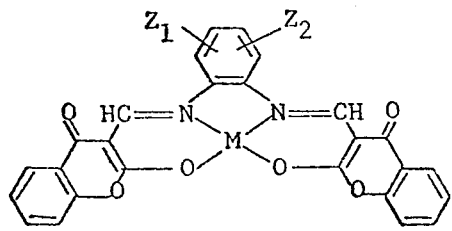

wherein $Z_1$, $Z_2$ and M have the meaning indicated in claim 2.

4. Bis-azomethine metal complex colorants according to claim 3, characterised in that $Z_1$ and $Z_2$ denote hydrogen, trifluoromethyl or chlorine.

5. Bis-azomethine metal complex colorants according to claim 4, characterised in that M denotes nickel.

6. The dyestuff of the formula according to claim 3

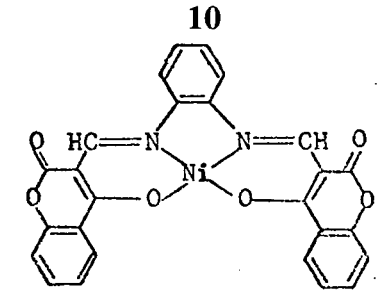

7. The dyestuff of the formula according to claim 3

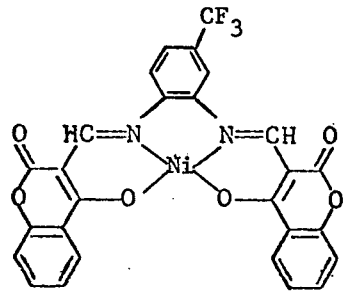

8. The dyestuff of the formula according to claim 3

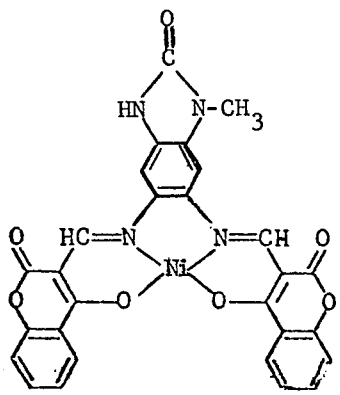

9. The dyestuff of the formula according to claim 3

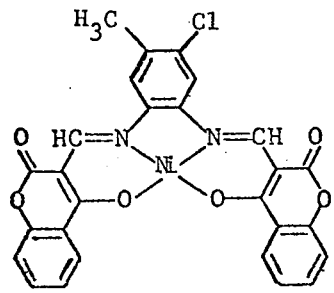

10. The dyestuff of the formula according to claim 3

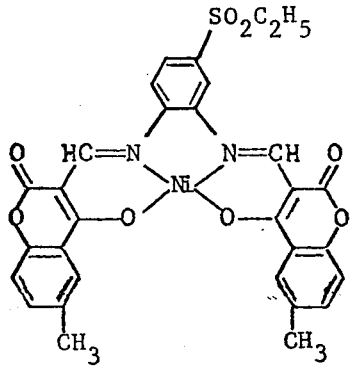

* * * * *